Figure 1:
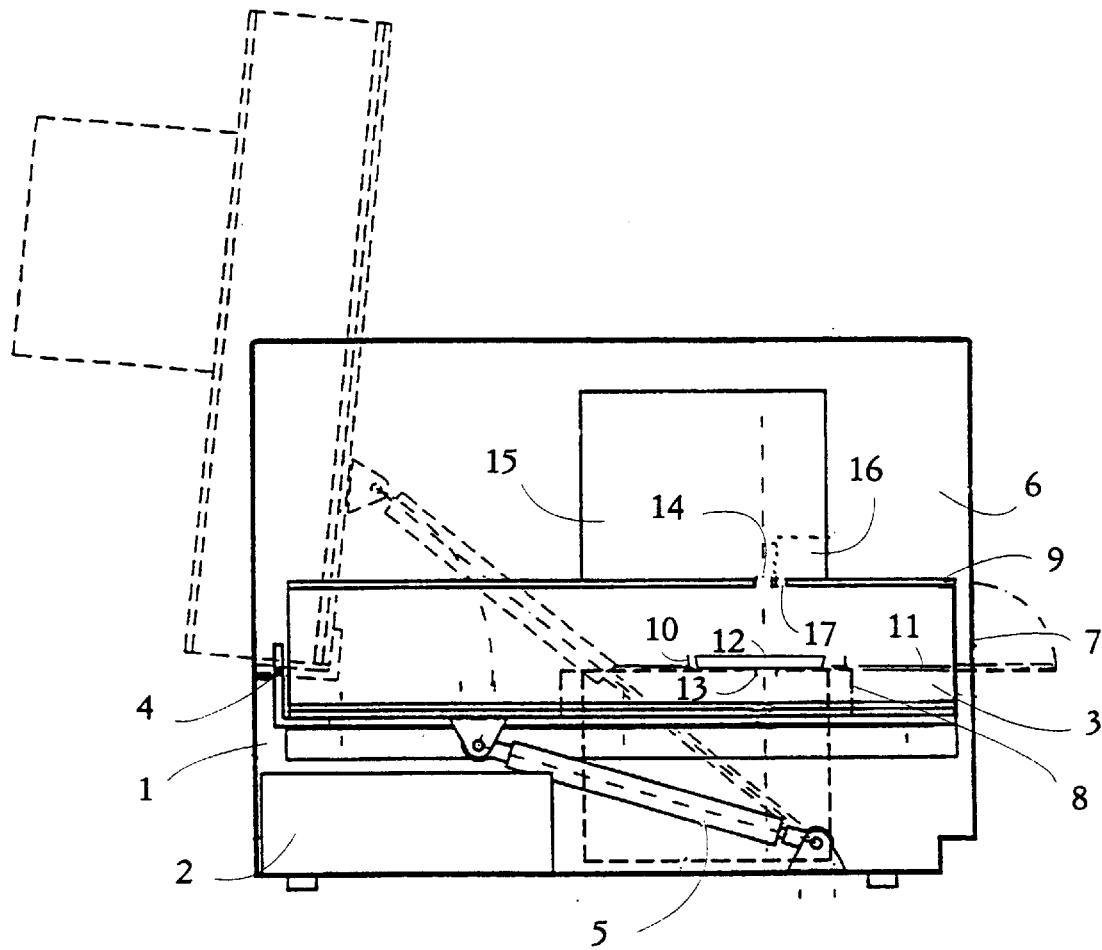

US005993746A

United States Patent [19]
Priha et al.

[11] Patent Number: 5,993,746
[45] Date of Patent: Nov. 30, 1999

[54] PLATE HOLDER

[75] Inventors: Matti Priha, Vantaa; Heikki Tupakka, Helsinki, both of Finland

[73] Assignee: Labsystems Oy, Helsinki, Finland

[21] Appl. No.: 09/043,710

[22] PCT Filed: Sep. 20, 1996

[86] PCT No.: PCT/FI96/00499

§ 371 Date: Mar. 20, 1998

§ 102(e) Date: Mar. 20, 1998

[87] PCT Pub. No.: WO97/11352

PCT Pub. Date: Mar. 27, 1997

[30] Foreign Application Priority Data

Sep. 22, 1995 [FI] Finland ..................... 954512

[51] Int. Cl.⁶ .......................... G01N 21/01; G01N 21/13
[52] U.S. Cl. ..................... 422/104; 422/63; 422/65; 436/43; 436/47; 436/49; 436/165; 356/244
[58] Field of Search ................. 422/104, 63, 66, 422/99; 436/46, 43, 47, 49, 165; 356/244

[56] References Cited

U.S. PATENT DOCUMENTS

| | | |
|---|---|---|
| 4,772,453 | 9/1988 | Lisenbee ................... 422/52 |
| 4,791,461 | 12/1988 | Kishimoto et al. ............ 356/446 |
| 4,900,148 | 2/1990 | Doerr ....................... 356/244 |
| 5,075,079 | 12/1991 | Kerr et al. ................. 422/64 |
| 5,122,342 | 6/1992 | McCulloch et al. ........... 422/65 |
| 5,337,140 | 8/1994 | Higiwara et al. ............ 356/237 |
| 5,592,289 | 1/1997 | Norris ..................... 356/244 |
| 5,595,710 | 1/1997 | Van Dusen et al. ........... 422/104 |
| 5,842,582 | 12/1998 | DeStefano et al. ........... 211/60.1 |

FOREIGN PATENT DOCUMENTS 0 231 951   8/1987   European Pat. Off. .
WO 92/22801  12/1992   WIPO .

*Primary Examiner*—Long V. Le
*Attorney, Agent, or Firm*—Fish & Richardson P.C.

[57] ABSTRACT

A holder for sample-holding plates has a retainer for pressing a plate placed in the holder both against the back wall and against a side wall. Thus a plate of a certain type will always settle in the same position in the holder. It is also possible to use in the holder plates of many sizes, which can be kept in place during handling owing to the retainer. The device is suitable for use in particular in assay methods in which samples to be assayed are handled on plates having a plurality of wells, for example in optical analyzers or other apparatuses.

24 Claims, 6 Drawing Sheets

PLATE HOLDER

FIELD OF TECHNOLOGY

The invention relates to laboratory technology and relates to a holder in which sample-holding plates can be handled. The invention is suitable for use in particular in assay methods in which the samples being assayed are handled on plates comprising a plurality of vessels, for example, optical analysers or dispensing devices.

BACKGROUND

Samples handled in laboratories may be in many types of vessels, according to need. For example, the diameters of the vessels vary from a few millimeters to a few centimeters. In general, larger entities, i.e. plates, are formed of the vessels. The plates also come in many sizes and shapes. The most commonly used plate is the so-called microtiter plate having 8×12 wells.

For the rationalization of assays it would be preferable if as many different types of plates as possible could be used in one and the same apparatus. In general, plates according to only a certain standard can be used in present-day apparatuses, such as optical analysers.

In certain optical analysers the sample-holding plate is handled in a holder in which the plate can be shifted over fractions of a millimeter in one given direction (e.g. iEMS Reader/Dispenser, Labsystems Oy, Finland). Thus it is possible to take into account small deviations from the standard of the outer dimension of the plate in the direction concerned. These apparatuses have in one edge of the plate holder adjustable stop screws, a movable wall, or a spring pressing against the plate.

DESCRIPTION OF THE INVENTION

General Description

A sample plate holder according to claim 1 has now been invented. Preferred embodiments of the invention are stated in the other claims.

The first object of the invention is a sample plate holder having a retainer for pressing the plate against both the back wall and a side wall of the holder. Thus a plate of a certain type will always settle in precisely the same position in the holder. It is also possible to use plates of many types in the holder, and owing to the retainer they can be caused to remain in place during handling.

The retainer preferably has a spring which presses the plate against the walls.

The holder can be used, for example, during the dispensing, mixing, reaction, washing or measuring steps of assays.

According to one preferred embodiment, the holder is mounted in a movable carrier in the handling apparatus. The handling apparatus is preferably one in which samples on different types of plates can be handled. By means of the carrier the sample-holding vessels are taken into the handling position, for example for the dispensing or removal of liquid, or for the carrying out of an optical measurement. By suitable movement of the carrier, the samples may, when so desired, also be agitated. A so-called scanning measurement can also be performed by moving the carrier.

According to one preferred embodiment, the movable carrier has a particular loading position, at which the plate is placed in the holder. In this case the device preferably has a retainer releaser which prevents the retainer from pressing against the plate when the carrier is in the loading position. Thus it is easy to place a plate in the holder. The releaser may, for example have a stop fixed relative to the frame of the apparatus, against which stop the retainer impinges and turns away from the walls, when the carrier arrives at the loading position.

When necessary, an adapter installable in the holder can be used, in which the sample-holding plate is placed.

Another object of the invention is an optical analyser having a sample plate holder of the kind described above. The apparatus may be, for example, a fluorometer, a luminometer, a nephelometer, a photometer, or any combination of these. To enable measuring to be performed from below, the holder and the carrier have an open area so that measuring light can be obtained from each vessel, for measurement from below. The apparatus is preferably one in which the light emitted from the sample can be measured from either above or below, according to the need at any given time. The arrangement is particularly suitable for fluorometers or luminometers.

The invention is especially well suited for use in automated systems. The coordinate data of the wells in each plate being used can be programmed into the handling apparatus. The plate may arrive in the holder even in a rather indefinite position, but owing to the retainer the plate will always settle in the correct position. The plate may also be introduced into the holder by a horizontal movement if one edge of the holder is open, at least in the loading position.

DRAWINGS

Figure 2:
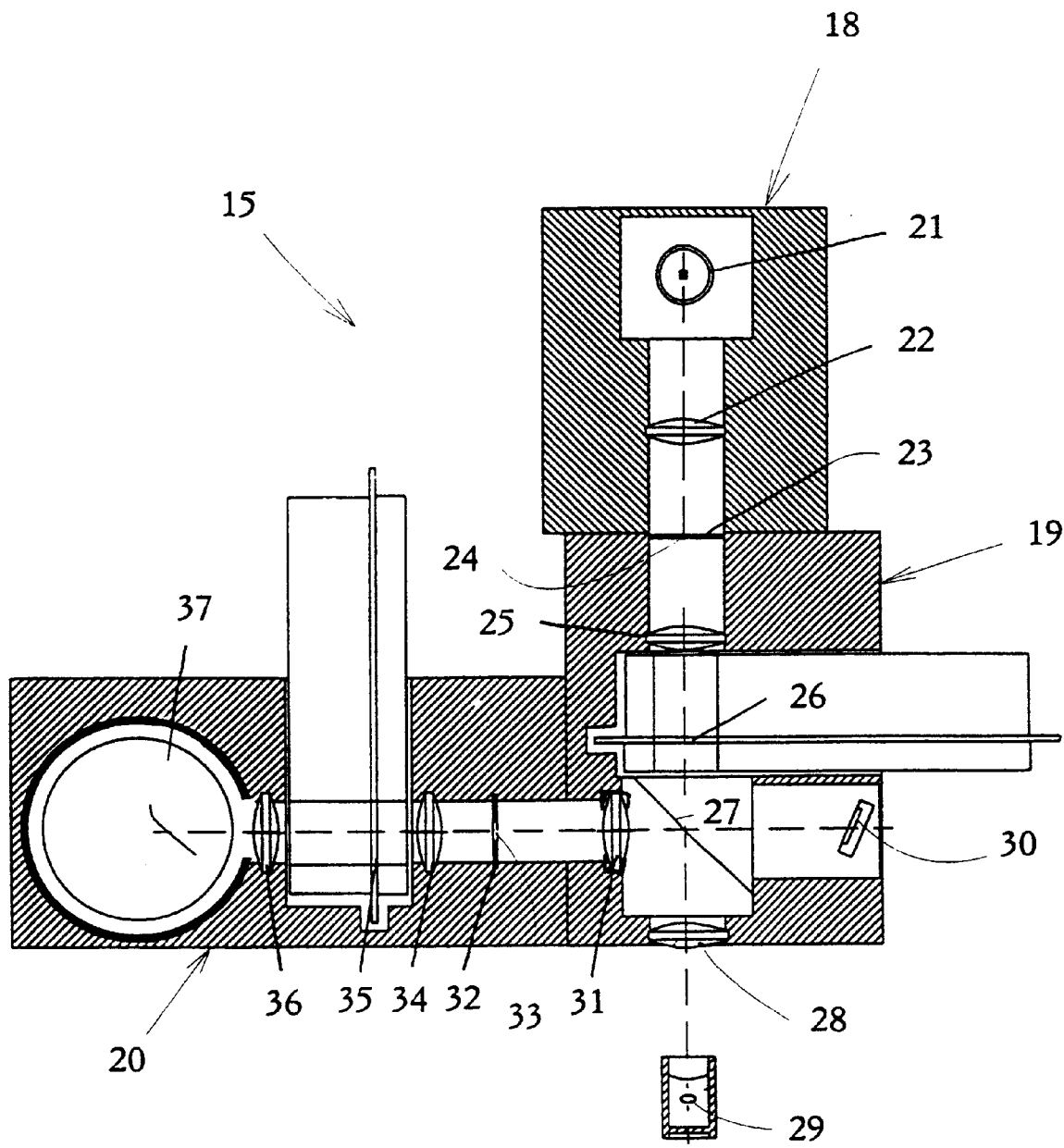
Figure 3:
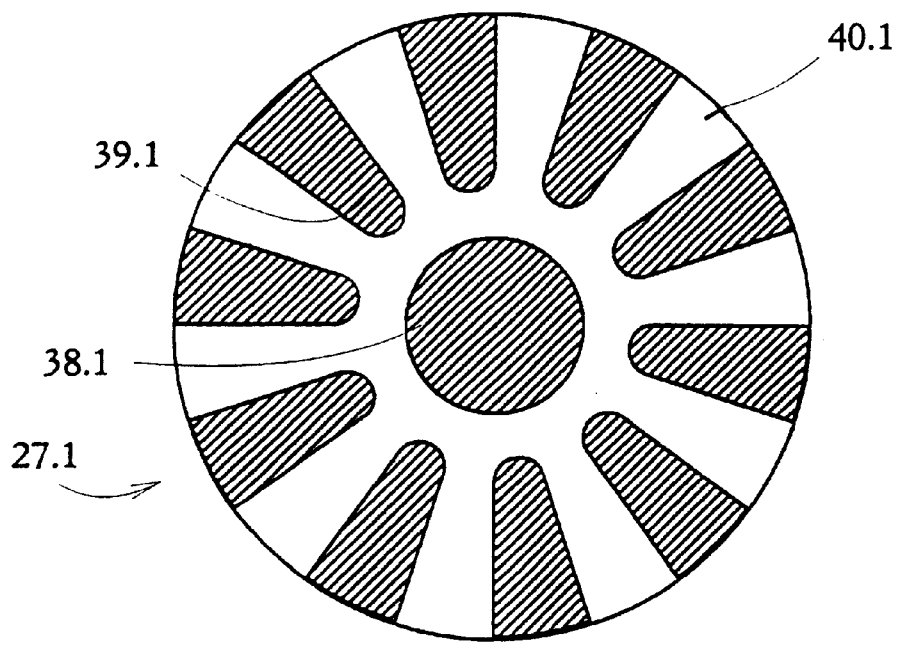
Figure 4:
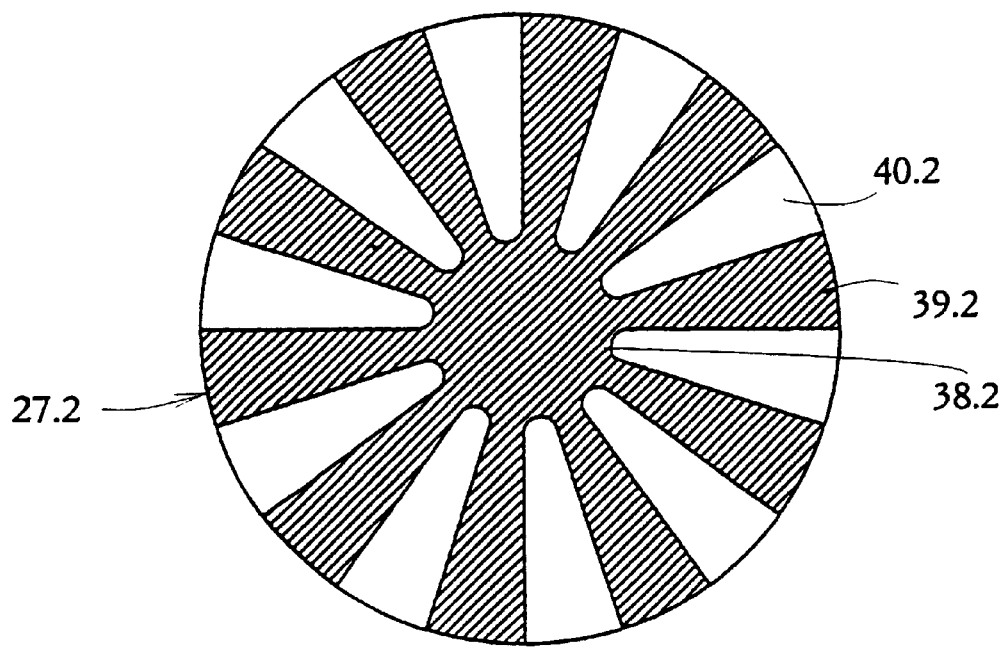
Figure 5:
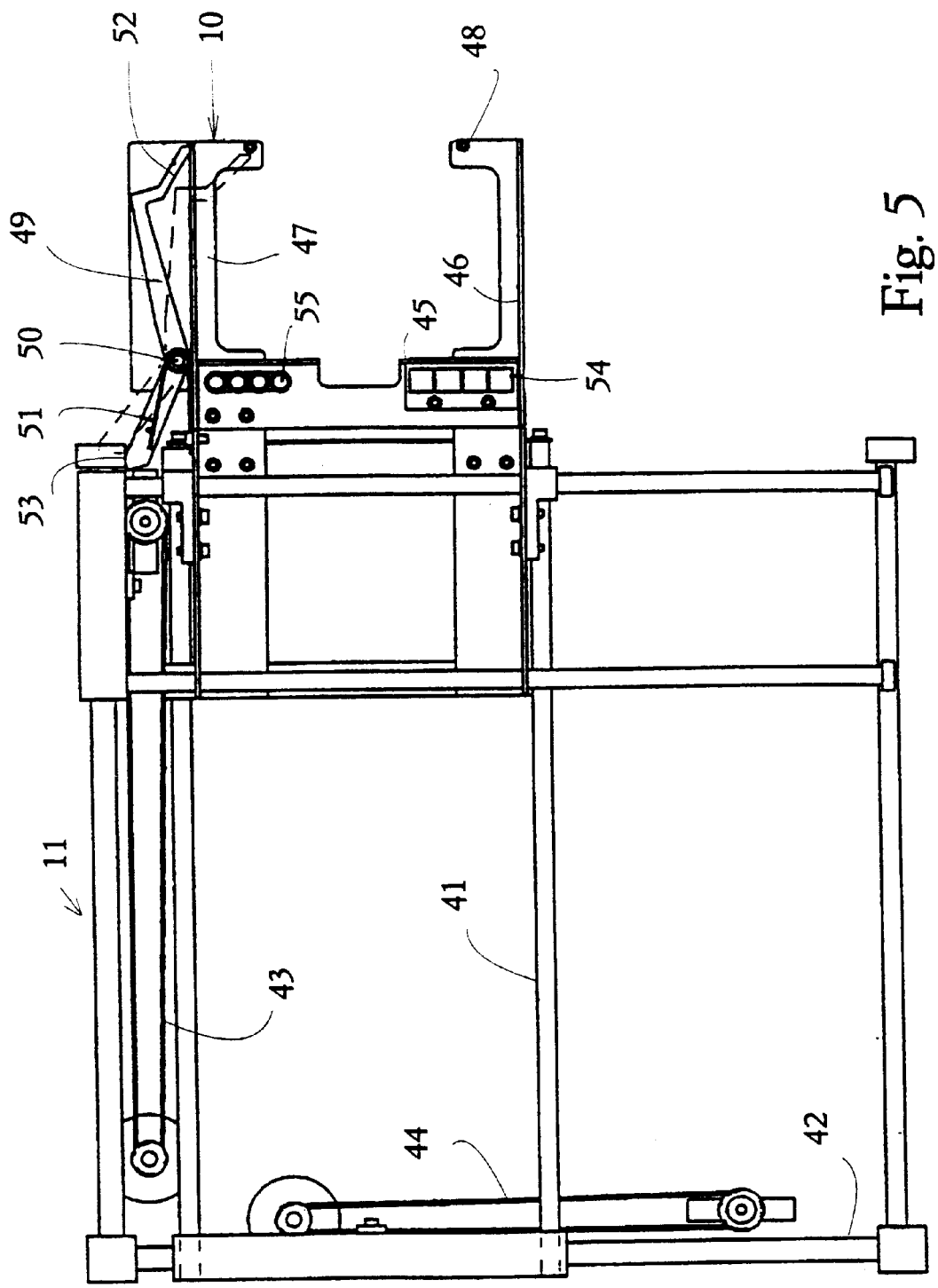
Figure 6:
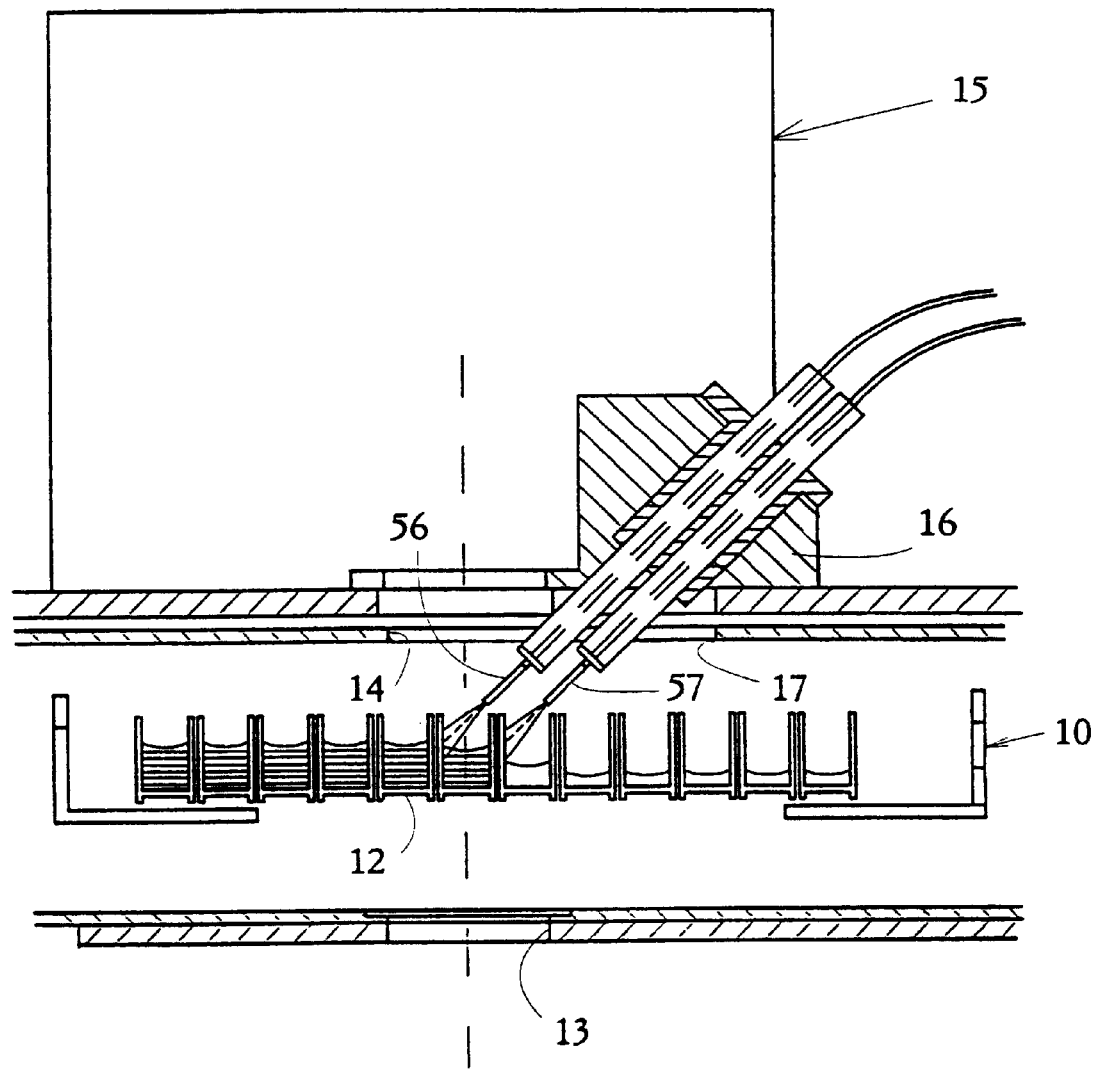
Figure 7:
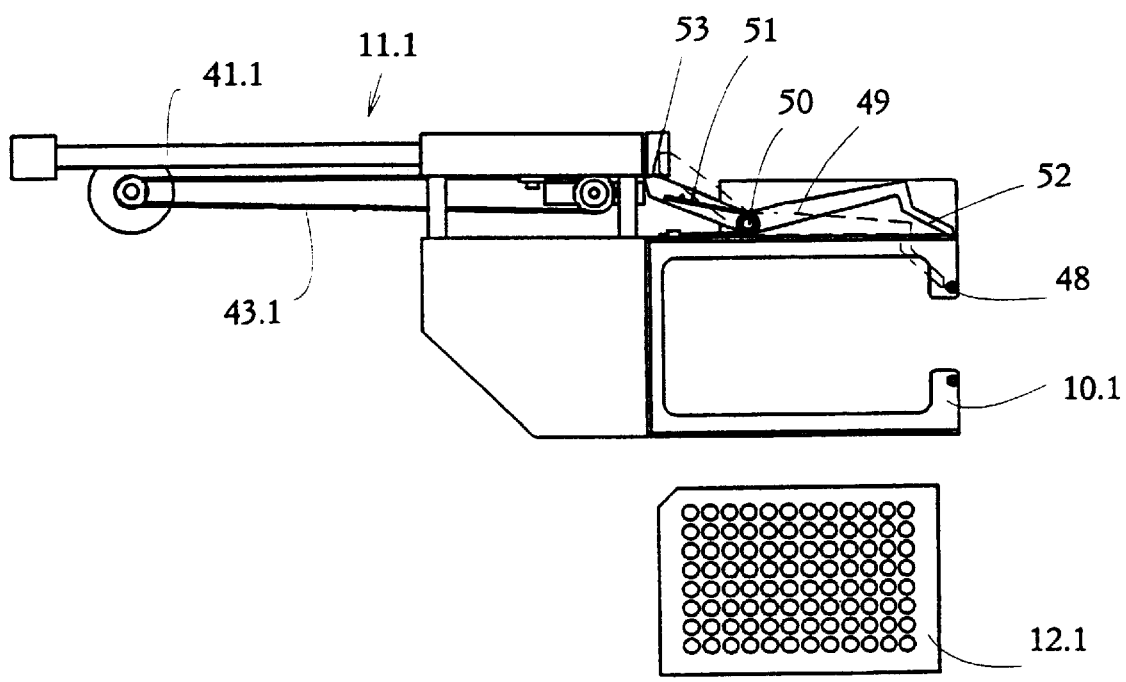

The accompanying drawings constitute part of the description of the invention. Therein FIG. 1 depicts a fluorometer having one sample plate holder according to the invention, FIG. 2 depicts the optics arrangement of the fluorometer of FIG. 1, FIG. 3 depicts one mirror usable in the optics arrangement, FIG. 4 depicts another mirror usable in the optics arrangement, FIG. 5 depicts a plan view of the sample plate transfer system in the fluorometer of FIG. 1, and FIG. 6 depicts a detail of the fluorometer of FIG. 1, with a plate in the dispensing and measuring position, and FIG. 7 depicts another transfer system.

SPECIFIC DESCRIPTION

The fluorometer of FIG. 1 has a lower housing 1 which houses, among other things, a control unit 2 and connections to the source of power and to functions external to the apparatus. On top of the lower housing there is a light-tight measuring unit 3. Its back edge is hinged 4 to the back edge of the lower housing so that the measuring unit can be pivoted upwards, whereupon there will be easy access to parts below it. The pivoted measuring unit is held in the upper position (shown by dotted lines in FIG. 1) by a pneumatic spring 5. Above the lower housing and the measuring unit there is a detachable upper housing 6. In the front wall of the measuring unit and the upper housing there is an aperture 7 equipped with a light-tight hatch, through which aperture samples are transferred into the measuring unit and out of it.

The measuring unit 3 has a lower deck 8 and an upper deck 9. In the space between these, a measuring carrier 10 is moved by transfer means 11. The plate 12 with the samples to be assayed is placed in the measuring carrier. The measuring carrier can be moved out through the aperture 7.

In the lower deck 8 of the measuring unit 3 there is a lower measurement aperture 13 and in the upper deck 9 an upper measurement aperture 14. The measuring unit has an optics module 15, which may be mounted either above or below the measuring unit. The upper deck additionally has a liquid dispensing unit 16 and a dispensing aperture 17, through which liquids can be dispensed into the wells of the plate 12.

The principal parts of the optics module 15 are a light source unit 18, a mirror unit 19, and a detector unit 20. The optics module is used for directing both excitation light to the sample and emission light from the sample, from either above or below.

The light source unit 18 has an incandescent bulb 21; an image of the filament of the bulb is converged by means of a lens system 22 to the aperture 24 of an excitation delimiter 23 in the mirror unit 19. It is preferable to keep the bulb switched on only during measuring, in order to increase its useful life.

The excitation light coming from the aperture 24 is collimated using a lens system 25, and the collimated light is directed through a filter 26 to a partly transparent mirror 27. By means of the filter the wavelength of the excitation light is delimited to the desired range.

The light which has passed through the mirror 27 is converged via a focussing lens system 28 to the sample. Thus a spot of light 29 is obtained in a delimited spatial region of the sample.

That portion of the excitation light which is reflected from the mirror 27 is directed to a reference detector 30. By means of it any errors caused in the measurement results by variation in the intensity of the excitation light are compensated for. A representative sample of the excitation light is obtained from the mirror. When one-half of the light is used for excitation, the other half can be exploited for defining the excitation amplitude. A unidirectional beam of light may be directed to a detector having a large surface area or, by means of a converging lens, to a smaller detector.

The emission light emitted from the spot 29 in the sample travels via the focussing lens system 28 to the lower surface of the mirror 27. From the portion reflected from the mirror, an image of the spot is formed, in the aperture 33 of the emission delimiter 32, by means of a converging lens system 31. From the aperture the emission light is collimated by means of a lens system 34 to a filter 35, from which it is directed via a converging lens system 36 to a detector 37. By means of the filter, the desired wavelength range is delimited from the emission light. The filter here is an interference filter. The detector is a photomultiplier tube.

When the mirror 27 is positioned close to the imaging lens system 28 common to the excitation channel and the emission channel, the image in the mirror is formed at a point far from the object being assayed. When the mirror is at a distance less than the focal distance, no image at all is formed.

The apparatus has a plurality of different excitation filters 26 and emission filters 35. The filters are mounted in a disc, and the desired filter is installed by rotating the disc. The filter discs are also replaceable.

The excitation delimiter 23 is replaceable, and thus an optimal excitation aperture 24 of the desired size and shape can always be placed in the module. The excitation light can thus be focussed, with a good efficiency ratio, precisely on the sample assayed at a given time, or on a preferred or sufficient region thereof. By means of the delimiter it is possible in particular to eliminate disturbances caused by the fluorescence of adjacent samples.

The shape of the delimiting aperture 24 may also vary according to the embodiment. For example, in certain embodiments the fluorescence of an electrophoretically formed line of the sample is to be measured. In such a case, a suitable linear aperture is used.

The user may also, when necessary, visually check the size and shape of the spot of light formed.

The emission delimiter 32 is also replaceable, and thus the light arriving at the detector can be delimited by means of an aperture 33. The light can always be measured from a precisely defined region. This can be used for minimizing background radiation arriving at the detector; such radiation may come in particular from the adjacent wells. The shape of the aperture can also be varied according to the samples to be assayed or their partial regions.

When desired, it is possible to use both an excitation delimiting aperture 24 and an emission delimiting aperture 33 for defining the size and the shape of the measurement region. Often the replacement of only one of the delimiters will suffice, since the disturbing adjacent sample is in any case located outside the area of the wider delimiting aperture. Preferably the excitation light region is made smaller than the emission measurement region.

The emission light treatment optics described can also be used for eliminating errors caused by variations in the distance to the object being assayed. Such errors may be caused, for example, by curvature of the plate, inclination of the path, and variations in the volume of the samples. Emission sensitivity can be made constant by making the solid angle of the measurement constant. This is achieved by means of an aperture delimiting parallel rays of light, positioned at a point after the mirror 27. In the embodiment of the figure, the retainer of the lens 31 serves as the delimiter. By suitable dimensioning, the depth effect can be almost entirely eliminated.

The light source unit 18 is also replaceable. In its place there can be installed against the delimiting aperture 24 the end of an optical fiber bundle by means of which excitation light is directed from an external source of light. In this case the image is formed of the end of the fiber bundle. This arrangement is used, for example, when a Xe bulb is needed, which requires special safety devices. The specific fluorescence of the fiber used for directing light does not cause problems here, since after the fiber the light passes through an excitation filter 26.

A usable partly transparent mirror 27 can be manufactured by forming reflective spots (diameter, for example, approx. 1 mm) on a glass sheet, these spots covering one-half of the optically transparent surface. The reflective material is preferably aluminum, which has a very wide reflection wavelength range (approx. 200 . . . 1500 nm). The glass sheet is preferably as thin as possible, which minimizes the amount of scattered light due to internal reflections in the glass.

Preferably, however, suitably shaped reflective areas are used. The reflective areas of the partly transparent mirror 27.1 in FIG. 3, the reflective areas are made up of a round center 38.1 and of separate radial sectors 39.1 around it, the transparent area 40.1 being respectively cartwheel-shaped. In the mirror according to FIG. 4, for its part, there is a continuous reflective area made up of a cartwheel-shaped center 38.2 and radial sectors 39.2 linked to it and of a transparent area formed by separate radial sectors 40.2. The central area minimizes the internal reflections of the optics. Owing to the edges of the radial reflective areas, diffraction of light can be caused to take place in the direction of a tangent transverse to the radius.

According to one embodiment, the mirror 27.1 or 27.2 is an oval the 45° projection of which is a circle.

In the transfer means 11 according to FIG. 5, the carrier 10 is mounted so as to slide along longitudinal slide bars 41, which in turn are mounted slidably on transverse slide bars 42. The slide bars can be moved by using motors and belts 43 and 44, and thus the carrier can be brought into the desired position within the measuring unit or out of the aperture in the front wall.

The carrier 10 is rectangular, and it has a back wall 45 and side walls 46. In the lower part of the side walls there are supports 47 so that an open space is left in the center. At the ends of the supports there are inward projections. At the front edge the projections have detachable vertical pins 48. The carrier 10 is dimensioned so that the plate for assaying can be placed to bear on the supports 47 so that the bottoms of the wells are left in the area of the opening. If the plate used is smaller than the opening, a suitable adapter tray is first placed to bear on the supports.

One side edge of the carrier 10 has a plate retainer 49. It is a lever having the basic shape of an obtuse V and being pivoted by its apex to a vertical pin 50 in the carrier. To it there is linked a spring 51, one end of which is against the frame of the carrier and the other end against the retainer so that it tends to turn the outer branch of the retainer towards the center of the carrier (in FIG. 5 clockwise). At the end of the outer branch of the retainer there is a projection 52 towards the carrier. When the retainer is in its released state it presses the plate in the carrier against the back wall and that side wall which is opposite the retainer. Thus the plates always settle in the carrier automatically in the same place against the corner. When the carrier is driven out of the measurement apparatus, the inner branch of the retainer impinges against a stop wall 53 in the transfer apparatus, the stop wall forcing the retainer to turn open. Thus a plate can be placed in the carrier or be removed from it. When the pins 48 are detached, a plate can be transferred to the carrier also along a horizontal path.

The back edge of the carrier 10 has four different fluorescent reference surfaces 54, by means of which the sensitivity of the detector can be checked when so desired.

FIG. 6 depicts the dispensing of liquid into a plate 12 in the carrier 10. From the dispensing aperture 17 there enter at an inward slant two dispensing heads 56 and 57. The first can be used for dispensing a liquid into a well at the measuring position and the second for dispensing a liquid into a well adjacent to the measuring position, in particular the one which will arrive next at the measuring position. In addition, the apparatus preferably has a third dispensing head, which can be used for dispensing a liquid into a well transversely adjacent to the measuring position (in FIG. 6 behind the well being measured).

The transfer apparatus 11.1 according to FIG. 7 has a carrier 10.1 movable by means of a belt 43.1 in one direction along slide bar 41.1. The apparatus has a plate retainer 49 similar to that in the apparatus according to FIG. 5.

The transfer apparatus 11.1 according to FIG. 7 can be used, for example, in multichannel photometers in which samples are assayed on a sample plate, such as a microtiter plate 12.1, one row at a time. Respectively the apparatus is suitable for dispensing devices in which liquids are dispensed onto a plate one row at a time.

We claim:

1. A holder for a sample-holding plate defining one or more sample-holding wells, said holder comprising a back wall and a side wall and defining a space between said back wall and said side wall into which a sample-holding plate can be placed, characterized in that said holder further comprises a retainer mounted to a holder frame for movement relative to said space between a first position for pressing a sample-holding plate placed in said space against both said back wall and said side wall and a second position retracted from pressing the sample-holding plate, said retainer comprising an arm defining a pressing surface disposed for pressing engagement with the sample-holding plate.

2. A holder according to claim 1, further comprising a spring mounted to urge said retainer toward said first position for pressing against the sample-holding plate.

3. A holder according to claim 1, wherein said holder is mounted in a movable carrier.

4. A holder according to claim 3, wherein said moveable carrier has a specific loading position at which the sample-holding plate is placed in the space of said holder or removed therefrom.

5. A holder according to claim 4, further comprising a retainer releaser adapted to urge said retainer toward said second position retracted from pressing the sample-holding plate when the moveable carrier is in its specific loading position.

6. A holder according to claim 5, wherein said retainer releaser is a stop defining a stop surface for engagement by said retainer in said second position.

7. An optical analyzer comprising a holder for a sample-holding plate defining one or more sample-holding wells, said holder being mounted in said optical analyzer and comprising a back wall and a side wall and defining a space between said back wall and said side wall into which a sample-holding plate can be placed, characterized in that said holder further comprises a retainer mounted to a holder frame for movement relative to said space between a first position for pressing a sample-holding plate placed in said space against both said back wall and said side wall and a second position retracted from pressing the sample-holding plate, said retainer comprising an arm defining a pressing surface disposed for pressing engagement with the sample-holding plate.

8. A fluorometer comprising a holder for a sample-holding plate defining one or more sample-holding wells, said holder being mounted in said fluorometer and comprising a back wall and a side wall and defining a space between said back wall and said side wall into which a sample-holding plate can be placed, characterized in that said holder further comprises a retainer mounted to a holder frame for movement relative to said space between a first position for pressing a sample-holding plate placed in said space against both said back wall and said side wall and a second position retracted from pressing the sample-holding plate, said retainer comprising an arm defining a pressing surface disposed for pressing engagement with the sample-holding plate.

9. An optical analyzer according to claim 7, wherein light from a sample can be taken for measuring from either above or below said holder.

10. An optical analyzer according to claim 9, said optical analyzer further comprising an optics module selectively positionable above and below said holder.

11. A holder for a sample-holding plate defining one or more sample-holding wells, said holder being mounted in a movable carrier and comprising a back wall and a side wall and defining a space between said back wall and said side wall into which a sample-holding plate can be placed, said holder further comprising a retainer mounted to a holder frame for movement relative to said space between a first position for pressing a sample-holding plate placed in said space against both said back wall and said side wall and a second position retracted from pressing the sample-holding plate, said retainer comprising an arm defining a pressing surface disposed for pressing engagement with the sample-holding plate, and said retainer having a basic shape of an obtuse V and being pivoted by its apex to a vertical pin in the moveable carrier, and said holder further comprising a spring linked to said retainer with a first end against a frame of the moveable carrier and an opposite second end against said retainer.

12. An optical analyzer according to claim 7, wherein said holder is mounted in a moveable carrier having a specific loading position at which the sample-holding plate is placed in said holder or removed therefrom, and said holder further comprises a retainer releaser adapted to urge said retainer toward said second position retracted from pressing the sample-holding plate when the moveable carrier is in its specific loading position.

13. An optical analyzer according to claim 12, wherein said retainer releaser is a stop wall defined by a stop and positioned for engagement by said retainer in said second position.

14. A holder according to claim 1, wherein a lower part of said side wall defines a support for the sample-holding plate.

15. A holder according to claim 14, wherein an edge of said holder is provided with detachable pins.

16. A holder according to claim 1, wherein said holder is adapted for use with sample-holding plates of different types.

17. A holder according to claim 1, further comprising a retainer releaser positioned to urge said retainer toward said second position, retracted from pressing the sample-holding plate.

18. A holder for a sample-holding plate defining one or more sample-holding wells, said holder comprising a back wall and a side wall and defining a space between said back wall and said side wall into which a sample-holding plate can be placed, characterized in that said holder further comprises a retainer mounted to a holder frame for movement relative to said space between a first position for pressing a sample-holding plate placed in said space against both said back wall and said side wall and a second position retracted from pressing the sample-holding plate, said retainer comprising an arm defining a pressing surface disposed for pressing engagement with the sample-holding plate, said holder being mounted in a moveable carrier and having a front edge opening into said space in a specific loading position of said moveable carrier at which the sample-holding plate is placed into said space or removed therefrom by substantially horizontal motion, and said holder further comprising pins detachably mounted at said opening for resisting placing or removal of the sample-holding plate in said space when the moveable carrier is removed out of its specific loading position.

19. A holder for a sample-holding plate defining one or more sample-holding wells, said holder comprising a back wall and a side wall and defining a space between said back wall and said side wall into which a sample-holding plate can be placed, characterized in that said holder further comprises a retainer mounted to a holder frame for movement relative to said space between a first position for pressing a sample-holding plate placed in said space against both said back wall and said side wall and a second position retracted from pressing the sample-holding plate, said retainer comprising a lever arm mounted for pivoting movement about a pin extending generally vertically from said holder frame.

20. A holder for a sample-holding plate defining one or more sample-holding wells, said holder comprising a back wall and a side wall and defining a space between said back wall and said side wall into which a sample-holding plate can be placed, characterized in that said holder further comprises a retainer mounted to a holder frame for movement relative to said space between a first position for pressing a sample-holding plate placed in said space against both said back wall and said side wall and a second position retracted from pressing the sample-holding plate, and sample-holding plate positioning and retaining means consisting of an arm mounted for movement relative to said space between a first position for pressing a sample-holding plate placed in said space against both said back wall and said side wall and a second position retracted from pressing the sample-holding plate, and a spring urging said arm toward said first position.

21. A fluorometer according to claim 8, wherein light from a sample can be taken for measuring from either above or below said holder.

22. A fluorometer according to claim 21, said fluorometer further comprising an optics module selectively positionable above and below said holder.

23. A fluorometer according to claim 8, wherein said holder is mounted in a moveable carrier having a specific loading position at which the sample-holding plate is placed in said holder or removed therefrom, and said holder further comprises a retainer releaser adapted to urge said retainer toward said second position retracted from pressing the sample-holding plate when the moveable carrier is in its specific loading position.

24. A fluorometer according to claim 23, wherein said retainer releaser is a stop wall defined by a stop and positioned for engagement by said retainer in said second position.

* * * * *